US007015032B2

(12) United States Patent
Adelberg et al.

(10) Patent No.: US 7,015,032 B2
(45) Date of Patent: Mar. 21, 2006

(54) INTERMITTENT IMMERSION VESSEL APPARATUS AND PROCESS FOR PLANT PROPAGATION

(75) Inventors: Jeffrey W. Adelberg, Clemson, SC (US); E. Phillip Simpson, Pickens, SC (US)

(73) Assignee: Clemson University, Clemson, SC (US)

( * ) Notice: Subject to any disclaimer, the term of this patent is extended or adjusted under 35 U.S.C. 154(b) by 21 days.

(21) Appl. No.: 10/809,187

(22) Filed: Mar. 25, 2004

(65) Prior Publication Data

US 2004/0209346 A1 Oct. 21, 2004

Related U.S. Application Data

(62) Division of application No. 10/110,866, filed as application No. PCT/US01/06586 on Mar. 1, 2001, now Pat. No. 6,753,178.

(60) Provisional application No. 60/186,191, filed on Mar. 1, 2000.

(51) Int. Cl.
*C12N 5/04* (2006.01)

(52) U.S. Cl. .................. 435/308.1; 435/410; 435/420; 435/431

(58) Field of Classification Search ................ 435/410, 435/420, 431
See application file for complete search history.

(56) References Cited

U.S. PATENT DOCUMENTS

| 3,856,946 A | 12/1974 | Debat |
| 5,141,866 A | 8/1992 | Levin |
| 5,505,716 A | 4/1996 | Simmet et al. |
| 5,514,119 A | 5/1996 | Curtis |
| 5,558,984 A | 9/1996 | Young et al. |
| 5,597,731 A | 1/1997 | Young et al. |
| 6,060,039 A | 5/2000 | Roe et al. |
| 6,066,748 A | 5/2000 | Han et al. |
| 6,190,913 B1 | 2/2001 | Singh |

FOREIGN PATENT DOCUMENTS

WO    WO 0134807    5/2001

OTHER PUBLICATIONS

International Search Report, PCT/US01/06586, 4 pages Aug. 6, 2001, Washington, DC.
International Preliminary Examination Report, PCT/US01/06586, 6 pages Feb. 1, 2002, Washington, DC.
Harris and Mason, "Two Machines For In Vitro Propagation of Plants in Liquid Media", Canadian Journal of Plant Science, 63:311-316.

*Primary Examiner*—Michele Flood
*Assistant Examiner*—Amy Lynn Clark
(74) *Attorney, Agent, or Firm*—Dority & Manning, P.A.

(57) ABSTRACT

A plant micropropagation apparatus and process is provided in which a support platform for vessels containing a liquid growth media are periodically pivoted which brings about an intermittent immersion of the plant tissue/growth substrate in the growth media. The motion of the support platform may optionally be used to engage a piston operated dispenser for supplying aseptic media to the sealed vessel. The intermittent immersion also provides for an improved method of separating viable embryos from culture materials using a separation matrix in conjunction with the intermittent wave motion of the plant media when suspended in a liquid culture.

4 Claims, 8 Drawing Sheets

INTERMITTENT IMMERSION VESSEL APPARATUS AND PROCESS FOR PLANT PROPAGATION

CROSS REFERENCE TO RELATED APPLICATIONS

This application is a divisional application of U.S. application Ser. No. 10/110,866 having a filing date of Apr. 18, 2002, Now Pat. No. 6,753,178, which is a national stage filing of PCT Application PCT/US01/06586 having a filing date of Mar. 1, 2001, which claims benefit of U.S. Provisional Application Ser. No. 60/186,191 having a filing date of Mar. 1, 2000.

FIELD OF THE INVENTION

This invention is directed to an improved method and apparatus for regenerating whole plants from calli or tissue. In particular, the invention is directed towards a novel process and apparatus for intermittently exposing the cultivated plant tissue to a growth medium. The invention is further directed to a novel method of separating cultured plant embryos on the basis of embryo size, shape, and density through the use of an intermittent rocking action in combination with a series of separation grids, sieves, and/or baffles.

BACKGROUND OF THE INVENTION

For many plant species there are well known protocols for the regeneration of whole plants from the aseptic culturing of an originally undifferentiated tissue such as protoplast, callus, or meristimatic tissue. Often, the protoplast, callus or meristimatic tissue have been genetically transformed or the meristimatic tissue is selected from a desired patented stock. The resulting protoplast, calli or tissue can then be regenerated into whole plants, including whole fertile plants that can grow in soil.

Existing methods of aseptic plant culturing involved starting with a callus or other stock material which is subcultured on a periodic basis onto a suitable fresh medium so as to induce embryo formation. As embryos are formed, they are removed and plated onto a second medium containing suitable plant growth regulators designed to bring about embryo maturation. Through periodic transfers onto fresh mediums, embryos can be differentiated into plantlets which are then transferred to another solid growth medium where root systems can be grown.

Alternative methods of plant regeneration or micropropagation involve the use of liquid cultures which immerse the various stages of the regenerating plant. While liquid culturing may be used to bring about mature viable plants, the process is expensive, prone to contamination, and requires that special steps be undertaken to successfully transfer the plants from a liquid culture environment to a condition where the plants are viable in a freestanding soil environment. In particular, the use of liquid cultures on rotary shakers results in a high shear force in the culture media. As vessel size increases, the high shear force involved in aeration creates an environment unsuitable for the growth and development of embryos and delicate organs such as leaves and shoots.

In particular, the collection and transfer of propagated embryos continues to be a labor intensive, manual process in which individual embryos are manipulated using forceps. While more mechanized solutions have been proposed, none have met with commercial success given in part the expense and complexity of the handling equipment.

It is also known in the art to propagate plant tissue into small plantlets as is taught in U.S. Pat. No. 5,597,731, incorporated herein by reference. The above patent discloses a plant propagation system in which sealed membrane vessels are used as a container for a plant material therein. The translucent vessels are permeable to gas and liquids. They are suitable for cultivating plant tissue obtained from a parent plant and which is subsequently grown heterotrophically. Once the plant material has developed the capability to photosynthesize, the sealed vessels are transferred to a greenhouse environment for photoautotrophic growth. An appropriate amount of needed gases, water, and liquid nutrient solution can be supplied in a controlled manner to the vessel trays.

Other plant propagation systems are known which use a liquid nutrient solution as set forth in U.S. Pat. No. 5,558,984, incorporated herein by reference. While a liquid nutrient solution for propagation of plant tissue offers numerous advantages in the large scale and economical propagation of plants, there remains room for improvement and variation within the art.

SUMMARY OF THE INVENTION

The present invention recognizes and addresses various disadvantages and drawbacks of prior art constructions and methods.

Accordingly, it is an object of the present invention to provide a plant micropropagation system.

It is another object of the present invention to provide a new method for propagating plant tissue.

It is a further object of the present invention to provide a micropropagation system for automatically growing plant tissues which makes use of an intermittent exposure to a liquid nutrient solution.

It is a further object of the present invention to provide a mechanized system and process for promoting the heterotrophic growth of plant tissue in an aseptic environment.

It is yet an additional object of the present invention to provide for an improved process for collecting culture-grown plant embryos.

It is a further object of the present invention to use the intermittent wave motion established within a culture vessel and in combination with a mechanical separator to separate plant embryos from non-embryonic tissues on the basis of the embryo size, shape, and density.

These and other objects are achieved by providing a mechanized micropropagation system and process in which a pivoting platform is used to periodically immerse the plant tissue maintained in a sealed vessel to the nutrient media. The pivoting movement of the platform facilitates the growth of the plant such that the majority of the time the plant is not immersed in the growth media. Furthermore, the movement of the platform engages the head of a piston-operated pumping mechanism which is used to release nutrients from a storage vessel into the plant containment vessel. As a result, the propagated plants are more suitable for release into a soil environment and the plants are cultivated in a process which limits the likelihood of widespread contamination or cross-contamination from single nutrient source.

Additional objects of the present invention are provided by a process of separating plant embryos and/or providing an embryo enriched fraction from culture media comprising the steps of separating embryos from propagated tissue cultures; providing a vessel adapted for receiving aseptic tissue and media; placing within an interior of said vessel a separation matrix consisting of an innermost layer of a substrate, a template positioned upon said substrate, said template defining a plurality of openings therethrough and providing communication with said substrate, and, a screen positioned above the substrate, said screen defining a plurality of openings; introducing into said vessel a supply of cultured tissue containing embryos and a separation medium; establishing an intermittent wave motion to said separation medium and said tissue culture; separating a plurality of individual embryos from said culture, said plurality of embryos passing through said openings of said screen and said openings of said template.

These and other features, aspects, and advantages of the present invention will become better understood with reference to the following description and appended claims.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying drawings.

DETAILED DESCRIPTION OF THE PREFERRED EMBODIMENT

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features, and aspects of the present invention are disclosed in, or are obvious from, the following detailed description. It is to be understood by one of ordinary skill in the art that the present discussion is a description of exemplary embodiments only and is not intended as limiting the broader aspects of the present invention, which broader aspects are embodied in the exemplary constructions.

Figure 1:
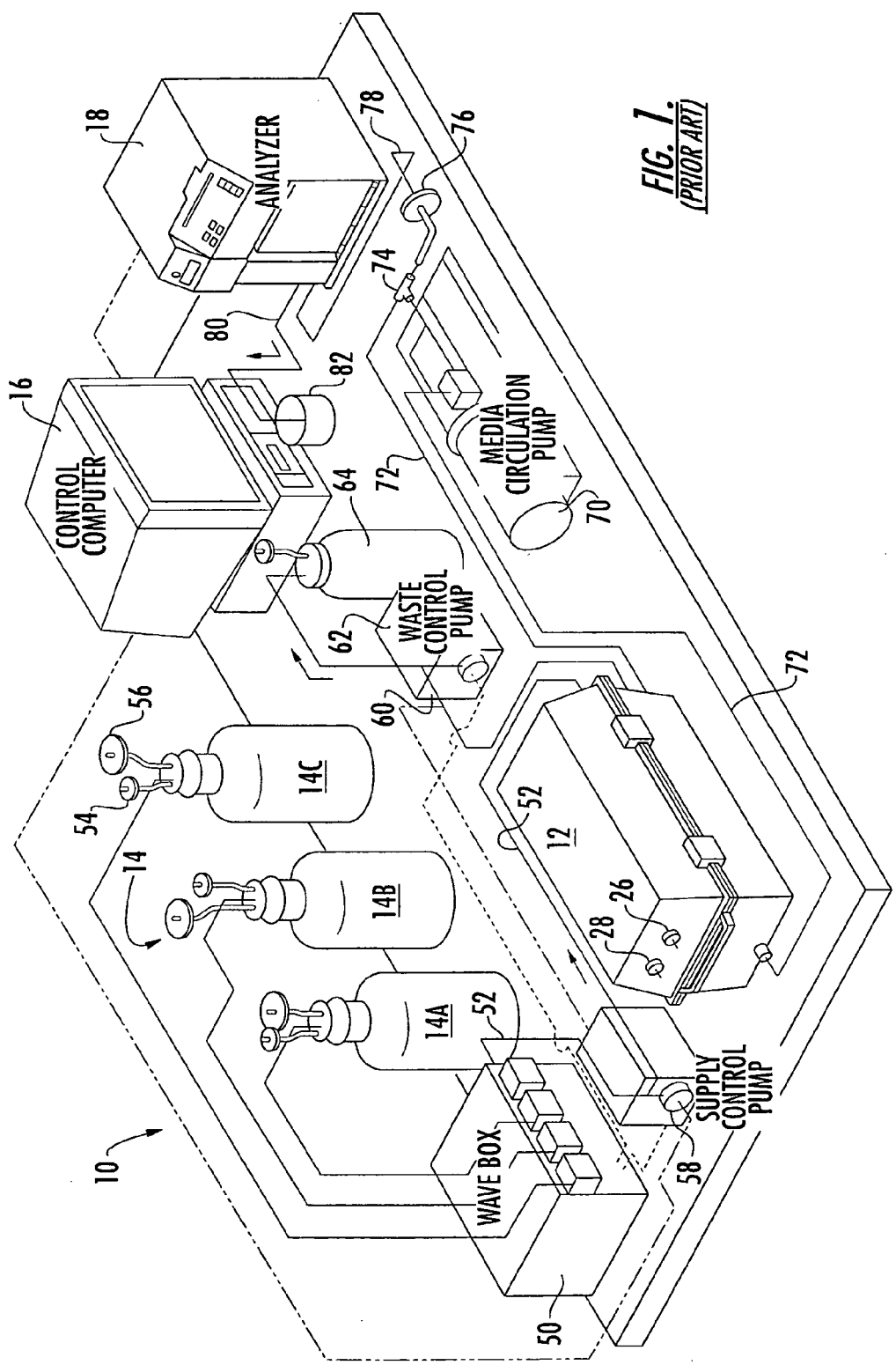
FIG. 1 is a prior art apparatus and process used in the micropropagation of plants as set forth in assignee's commonly assigned U.S. Pat. No. 5,558,984.

As seen in reference to FIG. 1, a prior art example is provided of a mechanized micropropagation system suitable for use with the present invention is illustrated. Generally, a micropropagation system 10 includes a vessel 12 where viable plant tissue is kept. Typically, the vessel 12 contains a substrate therein which supports the culture tissue. The substrate may be in the form of an agar, a membrane, a paper or textile mat, or other suitable support structure. A plurality of reservoirs generally 14 are connected to the vessel for supplying various solutions or subcomponents to the growing plant tissue. If desired, separate reservoirs can be provided for supplying various solutions such as a sucrose solution, a mineral salt and hormone solution, and distilled water. A controller 16 such as a microprocessor or computer in combination with a chemical analyzer 18 are also included for automating the system by controlling flow rates and by monitoring media concentrations and levels within the vessels 12.

One such suitable mechanized system for the heterotrophic growth of plant micropropagation via organ culture set forth in U.S. Pat. No. 5,558,984 which is incorporated herein by reference in its entirety. As seen in reference to FIG. 2, an improved support apparatus 100 for supporting a rigid vessel 12 is provided. Apparatus 10 includes a plurality of platforms 110 which provide a horizontal support which is periodically pivoted. As best seem in reference to FIG. 5, the pivoting action is brought about by coupling the platform 110 to a motor 112, which may have a variable speed, through a rocker arm 114. Rocker arm 14 is carried by a rotating cam member 116. The motor 112, by turning the cam 116, brings about the periodic movement of the rocker arm 114. The attachment of the second rocker arm end to the platform 110 causes the reciprocal side to side pivoting motion of the platform. As seen in reference to FIG. 5, cam 116 is provided with several spaced apertures which provide for varying attachment ports for the cam follower or rocker arm. These spaced attachment ports allow the operator to empirically determine the desired pitch angle for the intermittent motion. Preferably, the selection of the attachment port is integrated with the positioning of a switch 156, engaged by the moving platform, and which actuates the timer 152 and maintains elapsed cycle counts.

Figure 2:
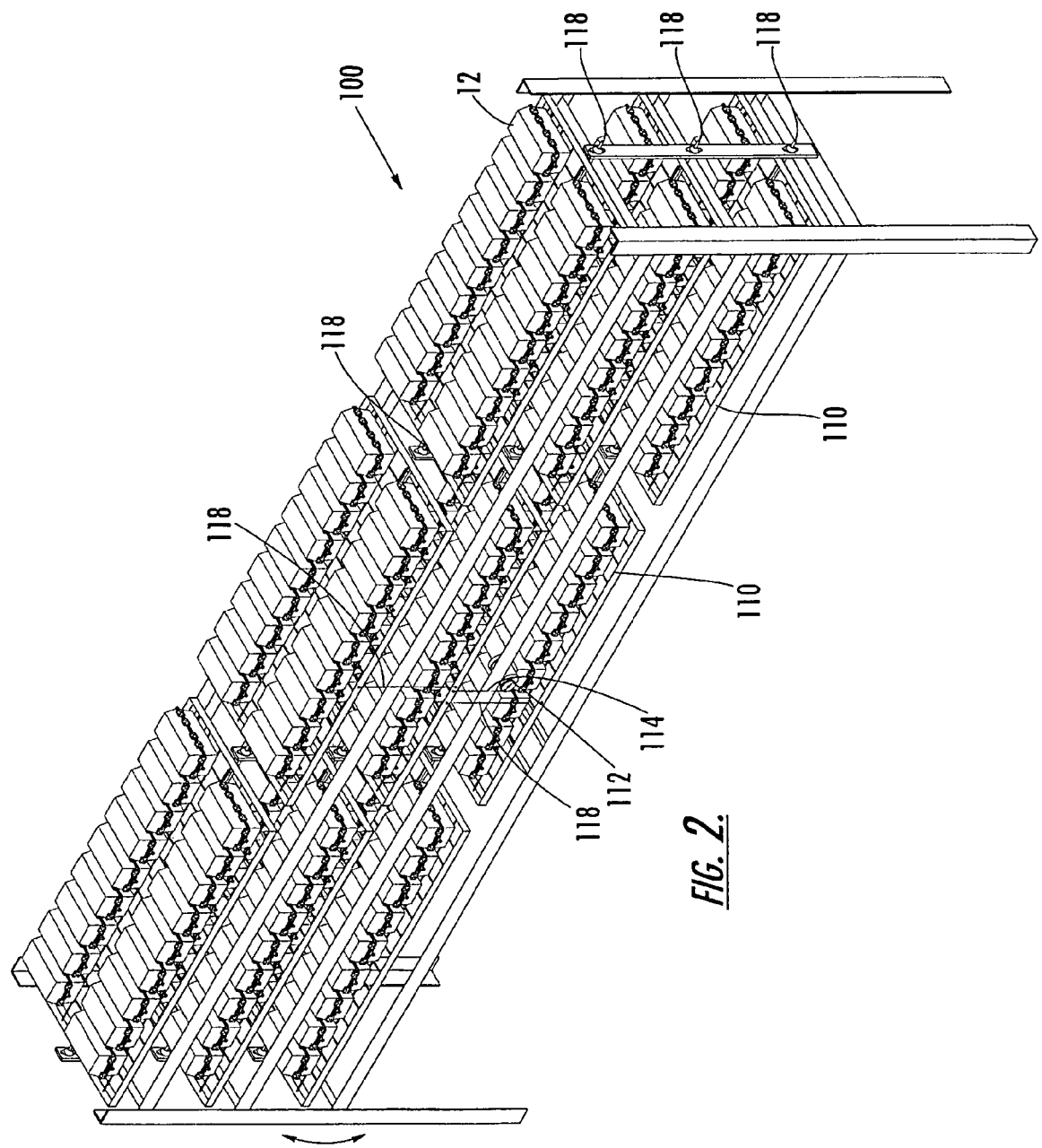
FIG. 2 is a perspective view showing a plurality of pivoting platforms which are interconnected with adjacent platforms and which are all operatively engaged by one or more motors, using linkage arms.
Figure 4:
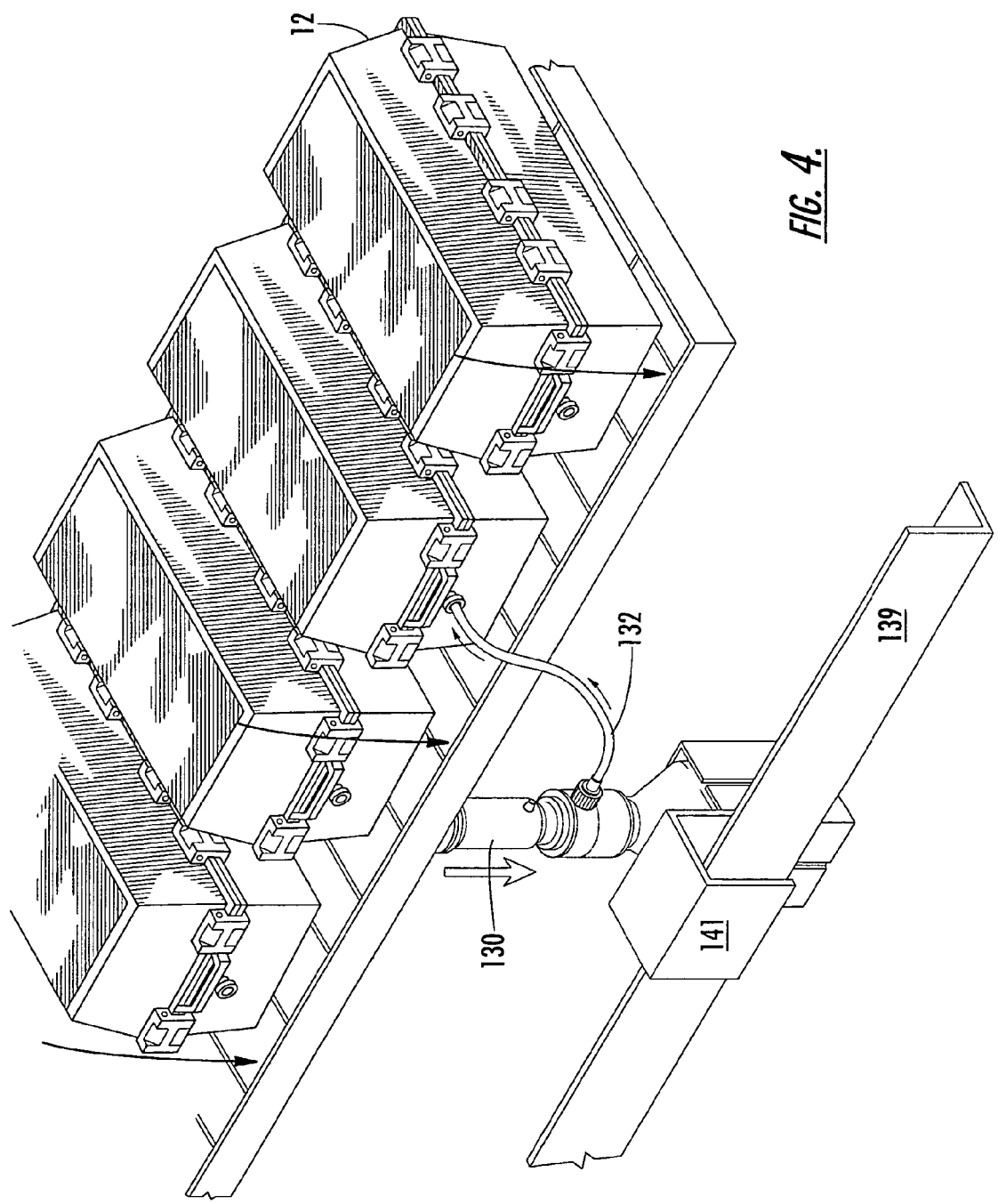
Figure 5:
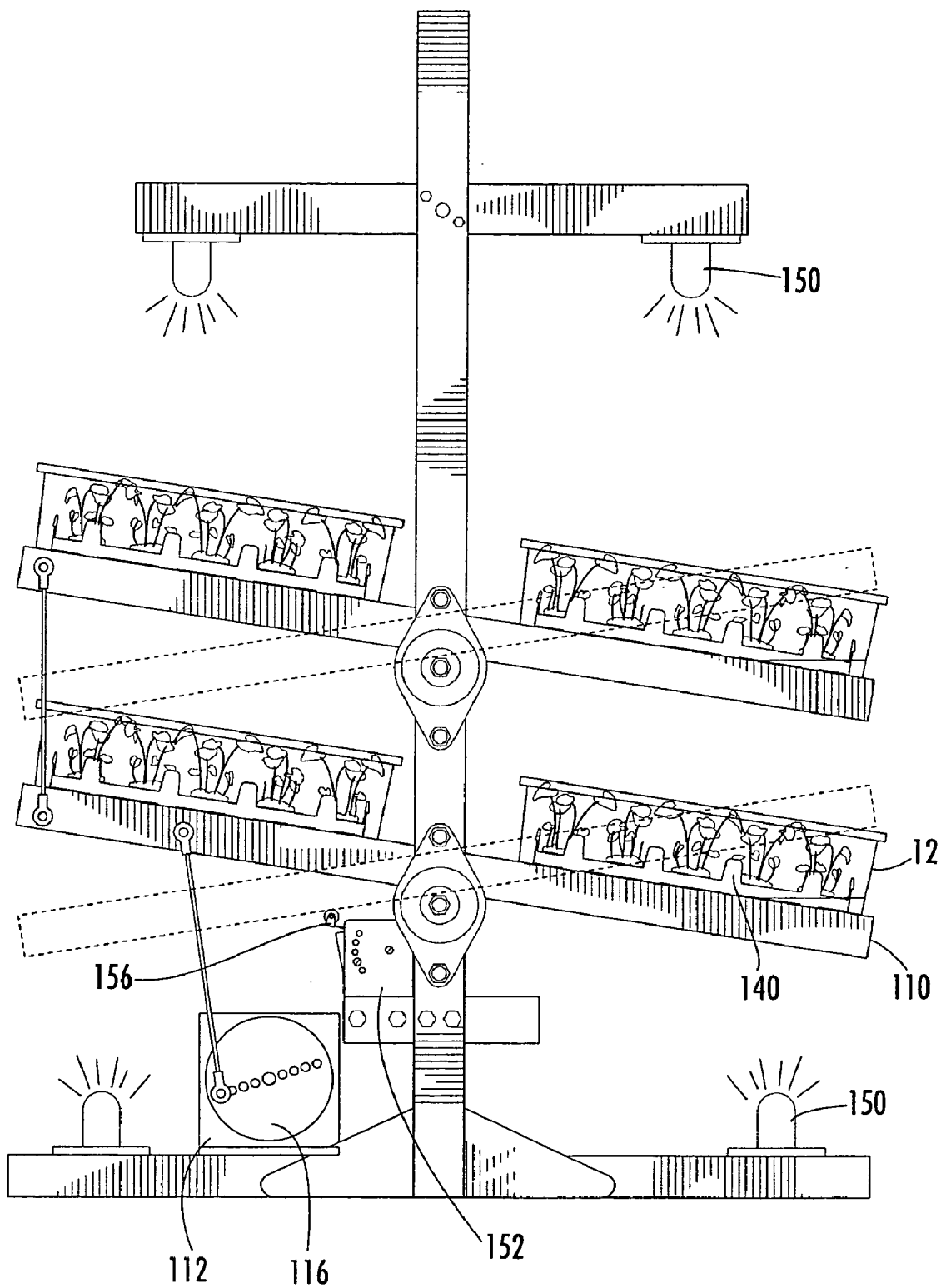
FIG. 5 is a side elevation view of a pivoting platform showing additional details of the pivoting motion brought about by linkage of the platform to a variable speed motor.

As best seen in reference to FIGS. 2 and 4, the platform 110 can support several culture vessels 12. Further, as seen in FIGS. 2 and 5, it is possible for a platform 110 served by a single motor to be physically interlinked to multiple rocker platforms via additional linkage arms 118 such that a single motor may be used to drive a plurality of platforms with a slow reciprocating movement. In reference to the embodiments seen in FIG. 2, each platform 110 pivots, as seen by the directional arrow, in a front-to-back rocking motion. A common pivot 118 is provided for each separate tier of platforms and extends the entire width of the apparatus 100. In this manner, a single motor may be used to bring about the intermittent motion of the 9-tiered platform, each platform capable of holding multiple vessels 12. This, in turn, saves costs associated with the motor operation and the initial capital cost associated with establishing a plurality of reciprocating platforms.

In operation, the motor 112 is responsive to a timing mechanism 152 which can be selected for a desirable time interval. Upon activation of the motor, the cam is rotated so that the cam arm is carried a desired distance along the rotating cam. The desired motion to the support platform may consist of a simple elevation of one edge of the platform which is then lowered to a substantially horizontal position. Thereafter, following a period of non-movement, the cam and cam arm are further moved which may be in the form of lowering the same edge of the platform and again returning the platform to a substantially horizontal orientation. If useful, it is, of course, appreciated that a complete cycle of up and down movement of the linkage arm may occur if such motion and resulting media flow is beneficial to the propagation process.

As further seen in reference to the above figures, a large number of platforms may be interconnected by a relatively small number of motors and associated linkage arms. Additional advantages offered by the illustrated embodiments herein include increased light transmission from bulbs 150 using a translucent platform surface. Improved lighting and a reduction of localized heating from the light tubes are additionally achieved by a platform surface which may be in the form of a wire mesh, metal or plastic support grids, or support rails. The use of the open grid or rail design allows greater light passage and heat dissipation through the entire propagation apparatus. As a result, fewer lights are required to illuminate the plant material when compared to the conventional non-light transmitting structures used with rotary platforms. The requirement of a reduced number of lighting sources and the increased ventilation also helps dissipate heat build up attributed to the light sources. As a result, electrical costs associated with lighting and maintaining a proper growth temperature are reduced.

Further reductions in cost are attributed to the intermittent activation of the rocker motors. The energy demands for the rocker motors, which operate only intermittently, are much reduced compared to a continuous operation of a rotary shaker platform apparatus heretofore used for tissue culture cultivation. Significant electrical cost reductions are attributed to the small electric motor used and the low speeds needed to bring about a high torque output. The electrical demands are associated only with the intermittent operation of the motor which is designed to induce movement of about 1 to 4 inches in a vertical motion so as to create a wave. In comparison, a typical rotary platform shaker has a large, high rpm motor with a large amount of inertia. As a result, the energy demands are much greater.

Figure 3:
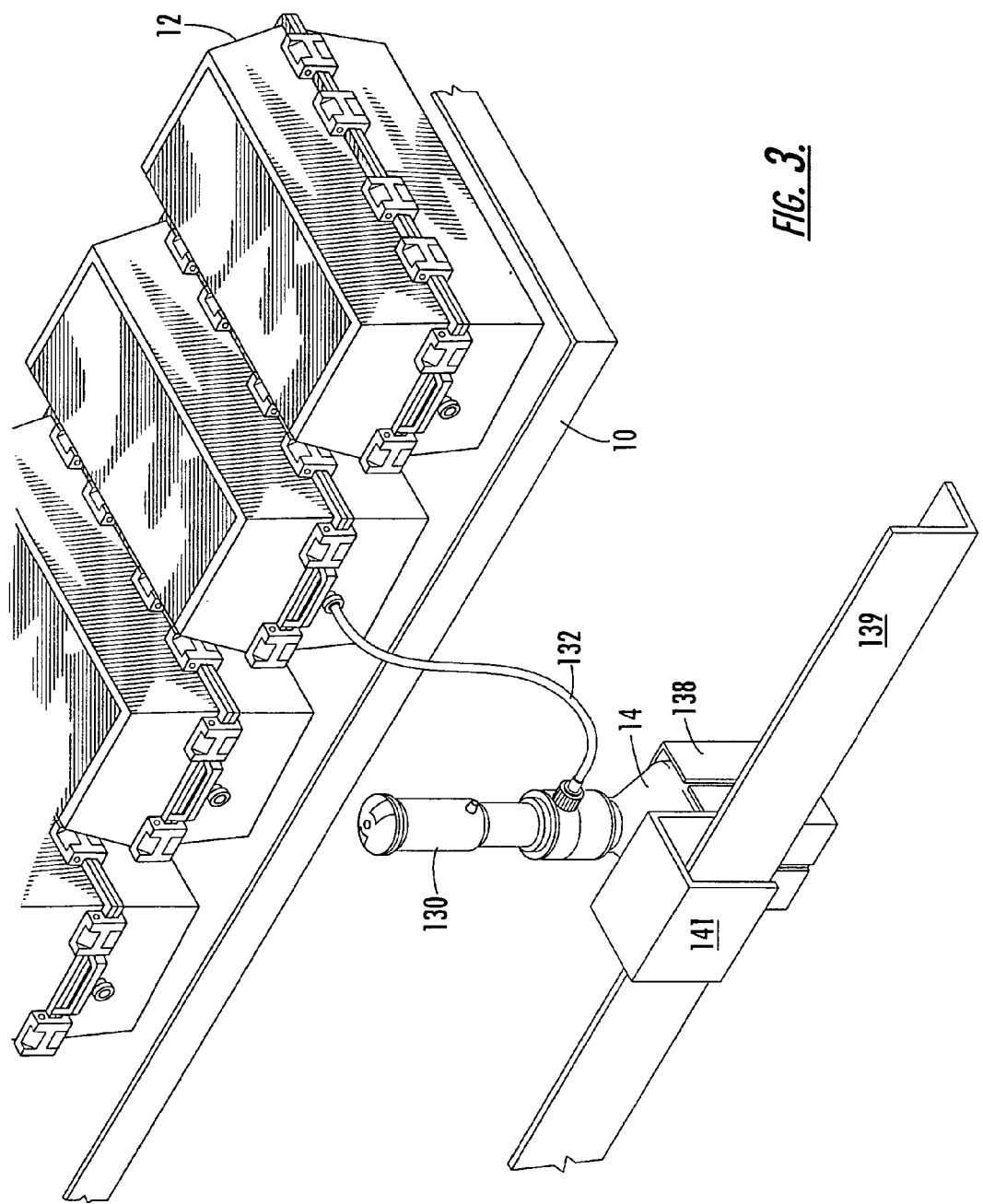
FIGS. 3 and 4 are perspective views of a plant culture vessel and platform in which movement of the platform is seen to engage a piston pumphead thereby dispensing media from the nutrient vessel to the plant culturing vessel.
Figure 7:
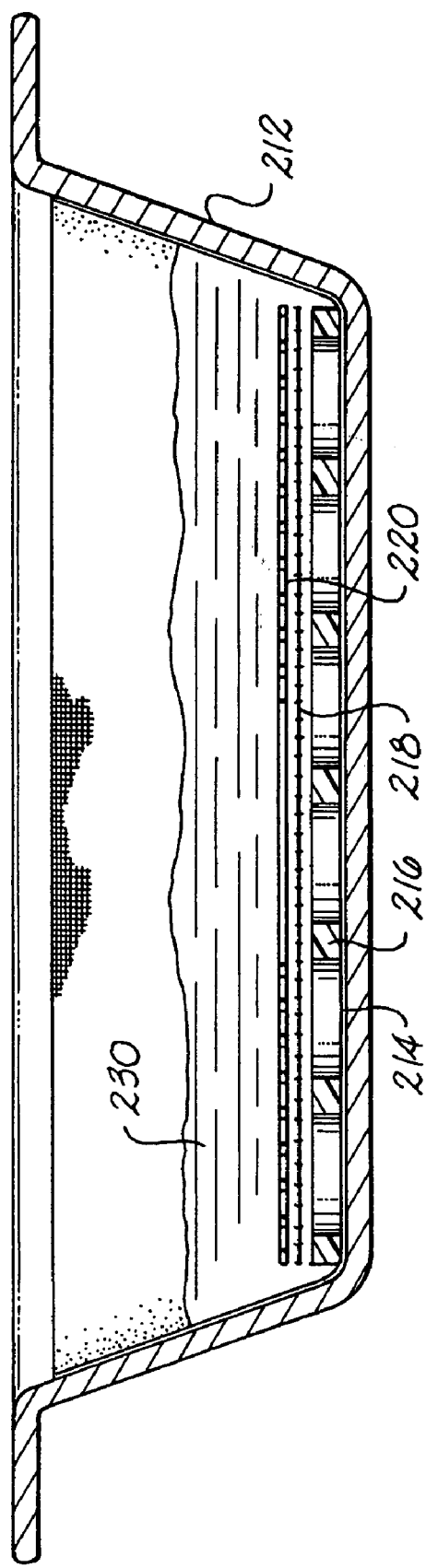
FIG. 7 is a side view of the apparatus of FIG. 6.

The present process and preferred embodiments offer additional advantages in the area of tissue culture and plant propagation. As best seen in reference to FIG. 7, each individual culture vessel 12 may be in an optional operative engagement with at least one nutrient reservoir 14. As best seen in FIGS. 3 and 4, a nutrient reservoir may include a piston pumphead 130 which is designed to aseptically dispense the vessel contents along the conduit associated with the vessel neck. The reservoir 14 and associate piston pumphead 130 is positioned within a holder 138 so that periodic downward movement of the rocker platform 110 will engage the pumphead 130, thereby automatically dispensing a metered amount of nutrient from the reservoir and into the vessel 12 along tubing 132. Holder 138 may be reversibly attached to an adjacent supporting rail 139 through an integral clip 141.

This arrangement allows each vessel 12 to have a separate nutrient supply reservoir 14. Dispensing of the nutrients is controlled by the physical interaction between the rocker platform 110 and the piston pumphead 130. This arrangement substantially reduces the risk of cross-contamination associated with a single nutrient supply being used to multiple vessels 12. Further, the mechanical action of the piston pump which is operated by the rocker panel greatly reduces the needs and associated cost of having separate pumps associated with the nutrient vessels.

The piston pumpheads 130 may be autoclaved, or otherwise sterilized to maintain the aseptic culturing conditions. A variety of well known and established aseptic techniques and materials may be used and adapted so as to ensure that introduced nutrients and the withdrawal of materials from the vessel 12 is carried out in an aseptic manner.

It has been found that the periodic immersion of the plants in the vessel 12 avoids the constant saturation of a non-pivoting platform. This, in turn, has been found to produce stronger, more uniform, physically robust plants which can thereafter be hardened and conditioned for growth outside the vessel.

For many types of plant propagation, it has been found useful to grow plants on a semipermeable substrate 140 (FIG. 5) which is raised above the floor surface of the vessel 12. This substrate, which may be of a membrane or paper composition, facilitates propagation of plants prone to hyper hydricity. The intermittent rocking action supplies nutrients as a liquid film which travels via capillary action along the raised substrate. In particular, the cultivation and regeneration of certain woody plant tissues is made possible using the raised substrate. The liquid films are intermittently replenished by the rocker action of the platform in which the liquid may be transferred by a wicking action of the plant bearing substrate. In this manner, the plants are able to grow in a non-saturated environment and results in a healthier, more robust plant stalk for handling and transfer to soil.

An additional advantage of maintaining separate nutrient supply vessels 14 is the ability to rapidly assay variations in nutrient and/or hormonal changes over a large number of vessels 12. Conventional propagation methods rely upon larger nutrient reservoirs which are difficult to manipulate or make use of small, flask-sized vessels which are time consuming to handle to bring about nutrient growth solution changes.

The present invention is also well adapted for rapid screening of contamination. The periodic intermixing of the liquid culture media allows a sample of the media within a vessel 12 to be withdrawn and assayed for contamination. Propagation methods using agar substrates are more time consuming to assay and the swabbing techniques do not provide for a thorough assessment of the culture conditions.

The addition of the rocker platform to a plant propagation system facilitates the growth of sturdier, hardier stock. Rather than floating along the surface of a nutrient solution, the intermittent exposure brought about by the rocker panel provides a more limited exposure to a liquid nutrient. As a result, a majority of the plant growth is occurring in a non-submersed root environment. This, in turn, more nearly mimics the soil conditions a plant would normally encounter and provides a resulting propagated plant which may be more readily transplanted to a soil environment.

The timing sequence of the rocker action may be on the order of a few minutes to several hours or more in duration. It is believed that the rocking action may offer an improved method of maintaining viable cultures of certain algae and seaweed associated with inter-tidal regions. Successful propagation of such tissues requires a periodic immersion which mimics the natural ebb and flow of tides. Conventional shaker or continuous agitation culture techniques are unsuitable for successful culturing of such species. Accordingly, the timing intervals and intermittent media immersion of the present invention offers the possibility of improved algal culturing techniques and similar improvements for other plant species which require intervals of desiccation.

The rocking action provided to the culture vessel 12 and contents also facilitate the rapid separation and transfer of embryonic and other tissue or organ initiating cells or aggregates. For instance, embryonic cell suspensions may be aseptically transferred en masse to the center of a vessel 12. The small embryos will randomly distribute themselves in a desirable, uniform pattern as a result of the intermittent rocking action. Dense embryogenic cultures will continue to produce embryos deposited on the lower tiers of the separator stack. The resulting embryos may space through a solid member riddled with holes in direct contact with a substrate and then be cultured and propagated into the desired plants and plant tissues without any time consuming steps of manually spacing the embryo materials. Such a capability is not present in a conventional rotary platform incubation environment and represents an enormous cost savings in the labor cost of propagating plant tissues.

The present propagation system and apparatus also lends itself to the rapid harvesting of plant tissues. For instance, cultivated leaf and shoot material can be aseptically harvested from the vessels. Thereafter, the vessels can be resealed and appropriate growth media added to regenerate the harvested tissue. It has been found that several cycles of the growth and harvest cycle are possible using the present apparatus and process.

The present apparatus and process, while described in reference to plant propagation tissues, is not limited to such uses. Many of the benefits of the present apparatus and process also lend themselves to incubation of animal cells which may be grown on a variety of substrates. In such instances, the periodic rocking action of the platform may be used to maintain adequate moisture, nutrition, and oxygen content without the undesirable effects of a continuous motion incubator.

Further, the use of the rocker panel and associated piston operated supply vessels are compatible with existing control systems which are used to remove and/or filter media. Each nutrient supply vessel can be connected to or in communication with a suitable filter 134 so that any introduced media into the vessel 12 is free of contaminants.

Use of the pivoting platform enables use of the piston pumphead in conjunction with the movement of the rocker panel. This arrangement permits an elegant coupling of the desired rocker movement with the desired metered delivery of nutrients. These improvements are also compatible with many existing propagation systems. The process offers improvement in the art with respect to the overall simplicity, cost savings, and reduces the incidence of large scale cross-contamination. Further, existing waste removal and nutrient monitoring systems may be used in conjunction with the present invention.

An additional advantage of the propagation process is directed to the ability to propagate plants which are not immersed in a liquid medium. Rather, a substrate such as a paper or membrane is used to support the plant above the liquid media. In accordance with the invention, it has been observed that some plant cultures release chemical exudates some of which preferentially bind to the substrate material. As a result, useful exudates may be harvested through the elution of the exudates from the growth substrate.

Additionally, it is envisioned that the substrate may be modified with various affinity compounds as used in conventional chemical separation chromatography. Such affinity compounds can be used to enhance the binding and recovery levels of useful exudates. Various ionic charges and electrical charges may also be applied to the substrate to take further advantage of various affinity interactions between the substrate and materials released from the propagated plants.

Figure 6:
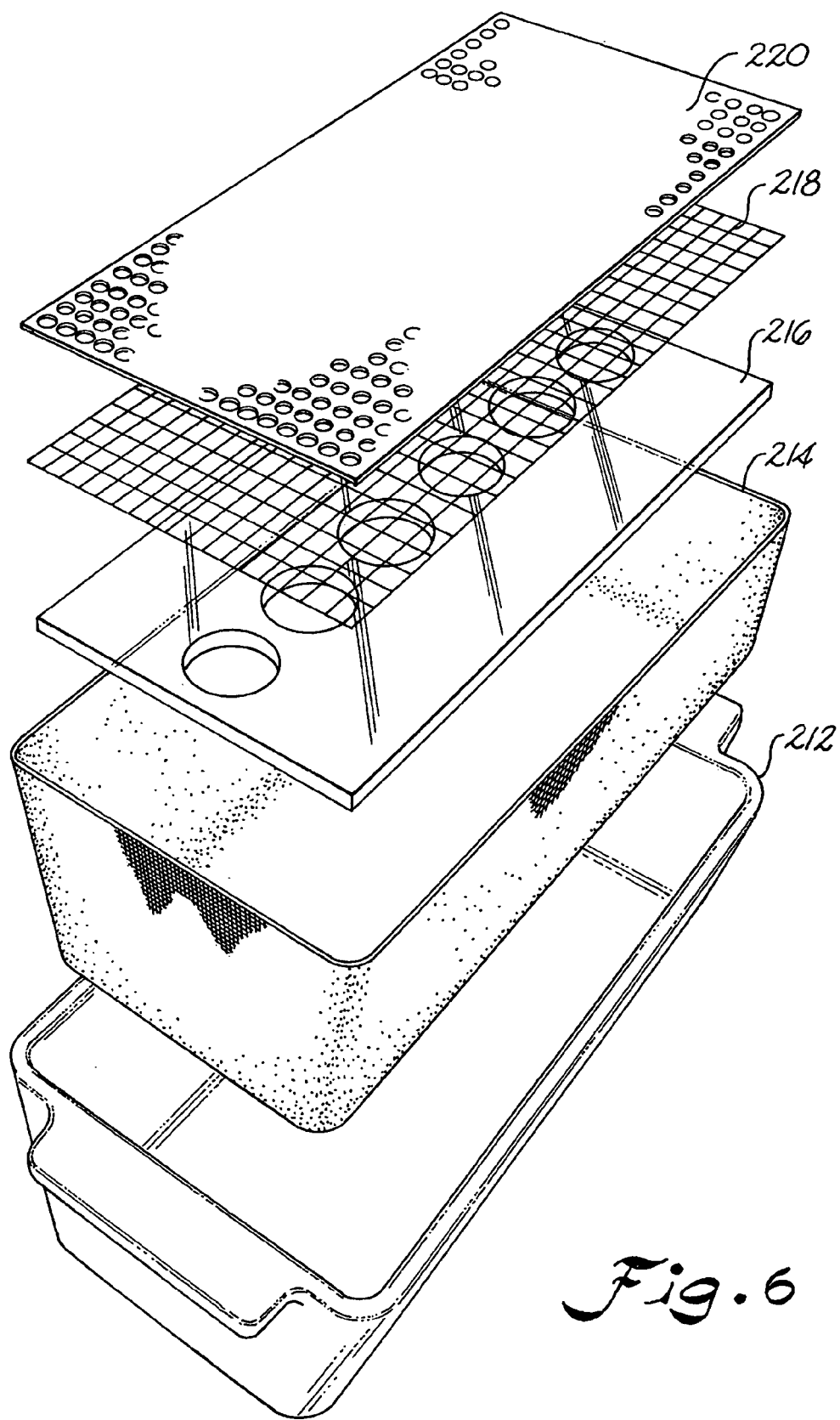
FIG. 6 is an exploded view of an embryo separation vessel illustrating the co-operating layers of separation material contained within the vessel.

The intermittent immersion process also lends itself to an improved process for isolating and collecting embryo enriched cell fractions from callus tissue and tissue suspensions. As seen in reference to FIGS. 6 and 7, the process may be carried out using a culture vessel 212 adapted for receiving sterile culture media and callus or cell suspensions. Preferably the vessel will maintain the viable cultures in an aseptic condition. The interior of the vessel contains a multi-layer separation matrix which has been found useful for isolating and separating embryos from propagated tissue cultures. The separation matrix makes use of the intermittent motion and wave action of the culture media and culture tissue to isolate and separate embryos based upon the embryo size, shape, and density.

The separation matrix takes advantage of the greater density of embryonic cultures. Embryonic cultures are also characterized by a smaller surface area and a characteristic torpedo shape. The intermittent wave-like oscillation movement of the culture vessel distributes the embryonic source material substantially uniformly across an upper screen 220. The upper screen 220 is designed to facilitate the release of smaller embryo-containing aggregates and serve as a physical barrier against passage of larger pieces of callus or other non-embryonic tissue. An additional lower screen 218 may also be present to provide additional separation and sizing capabilities.

The screen layers 218 and 220 may be provided from a thin mesh of polypropylene or fine chrome steel. Such materials are inert and are used by the food industry and are available in a variety of sizes and thicknesses.

Positioned beneath the one or more screen layers is a template 216. The template may be a plastic or metal sheet which defines a plurality of openings which may be in the form of a grid-like arrangement of a plurality of small, cylindrical apertures. The apertures may themselves be arranged in any number of useful patterns as referenced below. The template openings are preferably in the form of cylindrical apertures having an outer diameter of 1 to 6 mm. However, both the size and the shape of the template openings may be varied depending upon the characteristics of the target embryos.

The embryos pass through the upper screen layers 220 and 218, the screen layers excluding larger callus pieces. The embryos are subsequently suspended in the culture media present between the screens and the template. The continuing intermittent motion imparted to the separation vessel allows the embryos to circulate in this intervening media layer. From this layer, the embryos, being more dense than the separation medium, will pass through the template openings and come in contact with an innermost substrate layer 214 positioned beneath the template 216. The substrate layer may be provided by a piece of tissue paper or membrane. One such membrane is a nylon filter "Spectra Mesh™" (Spectrum product number 146502). This nylon filter mesh has an average mesh opening of 41 microns and has a thickness of 60 microns.

The embryos pass through the template openings and will engage the surface of the substrate 214. Once the embryos are received on the substrate, the embryos remain deposited on the substrate area defined by the outer walls of the overhead template. The selection criteria of size, shape, and density of the embryos results in the denser embryos making contact with the substrate.

Once adequate separation has occurred, the screen layers of the matrix, containing the lighter and/or larger fraction sizes of cell tissue may be removed from the vessel. The majority of the liquid culture media may also be removed by aspiration or other decanting methods. Subsequently, the thin template may be removed, the upper surface of the template removing an additional layer of tissue culture material which did not pass through the template openings. Upon removal of the template, the substrate now carries a discrete pattern of embryo-enriched material, the pattern of the deposited embryos conforming to the template openings.

At this point, the embryo enriched fractions supported on the upper substrate surface may be easily manipulated in a variety of post-harvesting steps. For instance, the embryos may be transferred en masse to a subsequent vessel for further incubation into plantlets. Additionally, the embryos may be used for subsequent gene manipulation and transformation studies. In this respect, one advantage of the separation technique is that the template may be designed to position the embryos in a grid-like pattern for subsequent treatment with a gene gun. Similarly, the template pattern may be selected for subsequent transfer of the embryos to greenhouse culturing conditions in which standard punches and dies may be used transfer portions of the substrate and embryos to containers having a desired spacing pattern.

A mesh-like substrate may also be used to form a pouch containing a desired number of embryos. The porous pouch may be used to contain the embryos while the embryos are subjected to various genetic transformation protocols, such as Agrobacterium transfection, which are well established in the art.

Figure 8:
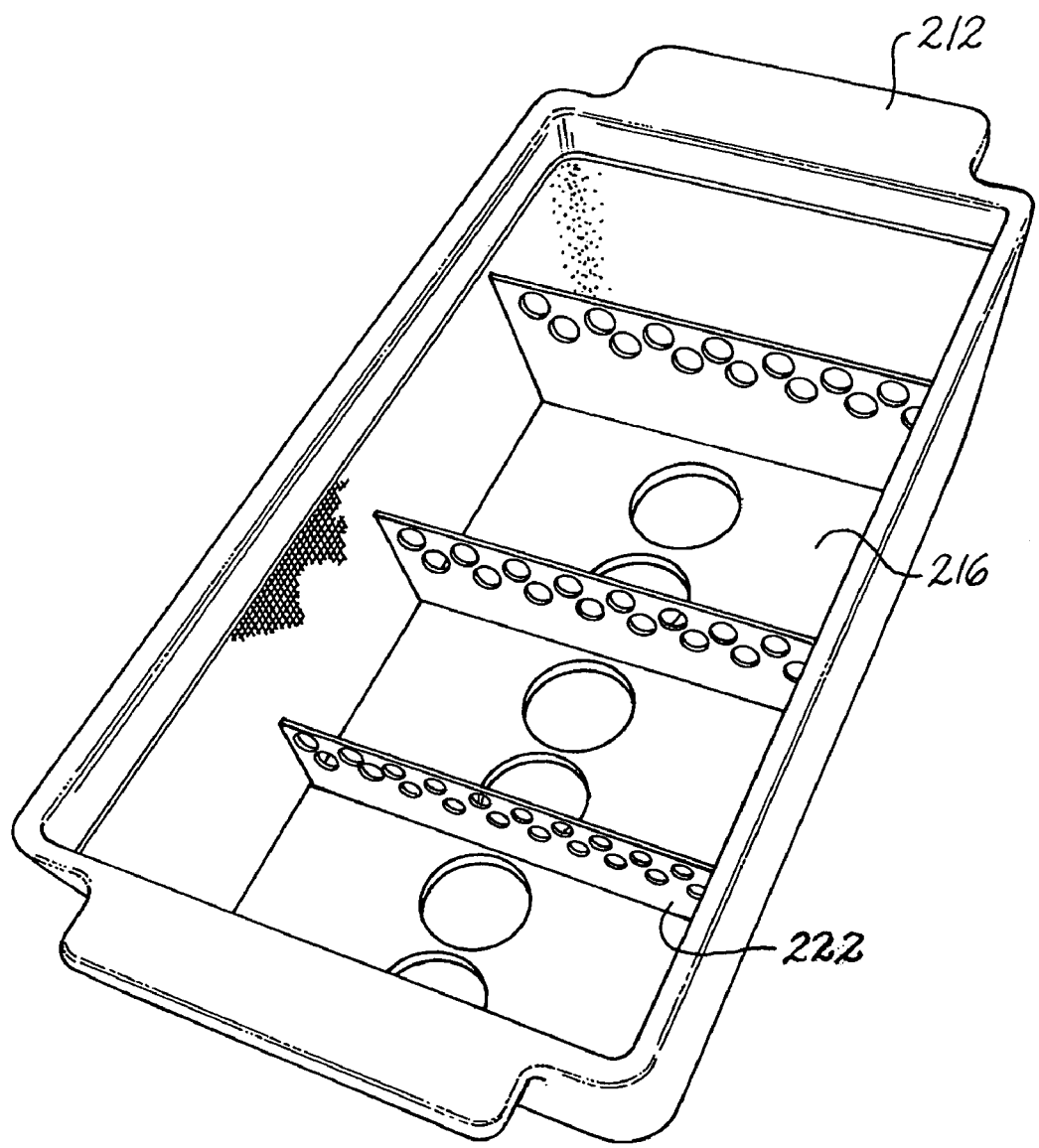
FIG. 8 is perspective view of an underlying substrate and separation layers used in the embryo sorting and oil extraction process.

The intermittent wave motion can also be used in conjunction with a different embryonic separation technique. As best seen in reference to FIG. 8, the separation vessel can be provided with a plurality of vertical baffles or dams 222 placed so as to intercept the actuated wave motion. The openings defined by the dam 222 serve as a selection mechanism which will allow only certain sized tissue to pass through. In accordance with this invention, it has been found that the use of small circular apertures can preferentially separate embryonic enriched fractions. As a result, starting culture material may be placed within one portion of the vessel which is separated from the remainder of the vessel by one or more dams. As the intermittent wave action is promulgated, the smaller, denser, and circular-shaped embryonic tissue may preferentially pass through the dam/baffle and accumulate in an adjacent region of the vessel. If desired, a gradation of smaller apertured dams may be used to further screen and select a desired size or stage of embryos within separate compartments of the vessel. As illustrated, it is envisioned that multiple baffles or dams 222 could be used to create various impoundments within the vessel. Further, a non-reciprocal stroke may be provided so that one side of the container is elevated higher than the other. The portion of the vessel closest to the highest side may be used to introduce the initial loading of cultured tissue. It is understood and appreciated that the height of the various dams, and the placement of the holes within the dams may be changed in both size and placement as the tissue is worked and processed along the slanted vessel. A substrate and template as previously described may be present on the bottom of the vessel, the substrate then being used to collect and transport the embryos upon removal of the liquid culture media.

The separation processes and materials described above may make use of the tissue culture media as the separation media. The use of a fine chrome steel material and the gentle oscillation motion maintains the viability of the tissue cultured source material. Consequently, following the separation, the non-embryonic cell fractions which remain may be reintroduced into culture media for further cultivation. Since the tissues remain viable, the duration of the separation protocol may be carried out over an extended time period. For instance, overnight separation protocols have found to be adequate when working with regenerated rice embryos. However, longer time intervals are quite possible. The minimum time duration needed for separation would, of course, vary depending upon the characteristics of the start material, the size of the separation vessel, the frequency of oscillations, and the materials used for the separation matrix. The appropriate separation time interval may be easily determined by routine evaluation using the protocols established above.

The use of an intermittent immersion bioreactor vessel may also be used to carry out chemical extractions from developed plant organs. In one aspect of the present invention, the gentle wave-like motion of the growth media allows advanced organs to be grown and suspended in a liquid medium. Organic exudates and similar released compounds may thereafter be extracted or decanted from the culture media used to suspend the embryos or other tissue during the intermittent incubation process. The gentle, intermittent wave action avoids damaging the living embryo and allows the embryo to naturally release materials into the media substrate which may then be collected and purified. Such a collection process is not possible with a typical rotary shaker in that the rapid orbiting velocity damages the cultured tissue and would subsequently result in the release of undesired proteases and wound reaction products. Such products would interfere with the desired collection of metabolic exudates.

An additional embodiment of an exudate extraction process involves the use of a two-phase suspension media. One phase may be the conventional growth or maintenance media used to maintain the cultured tissue. A second media may be of an oil-based liquid having a different density and maintaining a discrete phase separation from the tissue separation media. The suspension media is intermixed using the baffles and/or separation matrix described above. As a result of the intermixing, the tissue material, such as embryos, is exposed to the oil-phase media. In this manner, oil soluble exudates and compounds from the tissue may be released into the oil phase. The two-phase extraction process is sufficiently gentle that the normal metabolic processes of the cultured tissue are believed to be uninterrupted. Accordingly, useful metabolites, exudates, and oil-soluble extractables may be recovered by the oil phase. Following the separation interval, the two phases are allowed to separate. Thereafter, the oil phase may be withdrawn for recovery of various chemical fractions contained therein. Further, the tissue culture material may be rinsed and suspended under fresh culture conditions for further cultivation.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A process of separating oil soluble exudates and extractable materials from living plant tissue comprising:

supplying a source of cultivated plant tissue to a separation vessel;

introducing into said vessel a separation medium having at least two phases;

intermixing said two phases into a plurality of plates, said intermixing in response to an intermittent oscillation of said separation vessel;

exposing said plant tissue to said plurality of phase plates, thereby extracting from said plant tissue material oil-soluble exudates and extracts;

separating an separation medium into two phases; and, removing said oil phase containing said oil soluble exudates and extractions.

2. The process according to claim 1 comprising an additional step of introducing said plant tissue to fresh media following the removal of the oil phase.

3. A process of separating oil soluble exudates and extractable materials from living plant tissue comprising:

supplying a source of cultivated plant tissue to a separation vessel;

introducing into said vessel a separation medium having at least two phases, wherein at least one phase is a liquid oil phase;

intermixing said at least two phases, said intermixing occurring in response to an intermittent oscillation of said separation vessel;

exposing said plant tissue to said intermixed separation medium, thereby extracting from said tissue material oil-soluble exudates and extracts into said intermixed separation medium;

separating said separation medium into at least two phases; and, removing said oil phase containing said oil soluble exudates and extractions.

4. The process according to claim 3 comprising an additional step of introducing fresh growth media to said plant tissue following the removal of the oil phase of the separation medium.

* * * * *

UNITED STATES PATENT AND TRADEMARK OFFICE
CERTIFICATE OF CORRECTION

PATENT NO.      : 7,015,032 B2
APPLICATION NO. : 10/809187
DATED           : March 21, 2006
INVENTOR(S)     : Jeffrey W. Adelberg et al.

It is certified that error appears in the above-identified patent and that said Letters Patent is hereby corrected as shown below:

Col. 11, line 9 "thereby extracting from said plant tissue material oil-" should read --thereby extracting from said plant tissue oil--

Signed and Sealed this

Twenty-fifth Day of July, 2006

JON W. DUDAS
*Director of the United States Patent and Trademark Office*